(12) United States Patent
Burgess (10) Patent No.: US 7,637,900 B2
(45) Date of Patent: Dec. 29, 2009

(54) METHODS OF ADMINISTERING A MATERIAL INTO A PATIENT FOR DERMAL ENHANCEMENT

(76) Inventor: Cheryl Burgess, 7000 Oregon Ave., NW., Washington, DC (US) 20015

( * ) Notice: Subject to any disclaimer, the term of this patent is extended or adjusted under 35 U.S.C. 154(b) by 859 days.

(21) Appl. No.: 10/793,908

(22) Filed: Mar. 8, 2004

(65) Prior Publication Data
US 2004/0225276 A1 Nov. 11, 2004

Related U.S. Application Data

(60) Provisional application No. 60/453,966, filed on Mar. 13, 2003.

(51) Int. Cl.
*A61M 31/00* (2006.01)
(52) U.S. Cl. .................................................. 604/506
(58) Field of Classification Search ......... 604/500–510, 604/164.01–164.09, 272, 264, 46, 6.06, 6.05
See application file for complete search history.

(56) References Cited

U.S. PATENT DOCUMENTS

| | | | | |
|---|---|---|---|---|
| 5,241,969 A | * | 9/1993 | Carson et al. | 600/566 |
| 5,344,452 A | | 9/1994 | Lemperle | |
| 5,580,575 A | * | 12/1996 | Unger et al. | 424/450 |
| 6,306,425 B1 | * | 10/2001 | Tice et al. | 424/426 |
| 2002/0077277 A1 | | 6/2002 | Usala | |

FOREIGN PATENT DOCUMENTS

| | | |
|---|---|---|
| WO | WO 98/40027 | 9/1998 |
| WO | WO 99/11196 | 3/1999 |
| WO | WO 02/17816 A1 | 3/2002 |

OTHER PUBLICATIONS

The Science of Collagen, Collagen Corporation, Product Brochure, 8598-01-0695/2850-04-0595, 1994.
ADG needle: Enhancing Injection Technique, Collagen Corporation, Product Brochure, 8627-01-0695/2850-04-0595, No Date.
Zyderm® Collagen and Zyplast® Collagen Explained, Collagen Biomedical, Product Brochure, 2851-04-0595, 1995.
Treatment of Acne Scars, Collagen Biomedical, Product Brochure, 8534-01-0695/2850-04-0595, No Date.
Treatment of Glabellar Lines, Collagen Biomedical, Product Brochure, 8531-01-0695/2850-04-0595, No Date.

(Continued)

*Primary Examiner*—Manuel A Mendez
(74) *Attorney, Agent, or Firm*—Castellano PLLC; Kristina Castellano (57) ABSTRACT

The present invention is directed to methods of administering a material to a patient for dermal enhancement and/or as soft tissue fillers. The invention also relates to double-gloved methods of molding such a material after administration to a patient to achieve a desired orientation of the material in the patient. The invention also relates to the use of certain materials, including polylactic acid, hyaluronic acid, hydrogel, and/or collagen or other suitable materials for the preparation of a pharmaceutical composition for dermal enhancement and/or as soft tissue filler. The invention further relates to kits or packages that include a material for dermal enhancement and/or soft tissue filler and instructions as to how dermal enhancement or the filling of soft tissue is achieved.

9 Claims, 7 Drawing Sheets

OTHER PUBLICATIONS

Treatment of Nasolabial Lines, Collagen Biomedical, Product Brochure, 8442-02-0695/2850-04-0595, No Date.

Treatment of Oral Commissures, Collagen Biomedical, Product Brochure, 8441-02-0695/2850-04-0595, No Date.

Treatment of Periorbital Lines, Collagen Biomedical, Product Brochure, 8536-01-0695/2850-04-0595. No Date.

Zyderm® I With Fine Gauge Needle, Collagen Biomedical, Product Brochure, 8536-00-0194/2850-03-1192, No Date.

European Search Report, corresponding EP Patent Application No. 04718482.5—1219.

Elson, M. "Soft Tissue Augmentation Techniques: Update on Available Materials," Cosmetic Dermatology 12 (5):13-15 (1999).

Klein, A.W. "New Filling Substances on the Horizon," Cosmetic Surgery: An Interdisciplinary Approach (Marcel Decker, New York) Chapter 16, pp. 313-331 (2001).

Monheit, G. "Fibrel: Soft Tissue Augmentation," Tissue Augmentation in Clinical Practice: Procedures and Techniques Basic and Clinical Dermatology; 15 (Marcel Decker, New York) Chapter 8, pp. 155-171 (1998).

Klein, A.W. "Skin Filling Collagen and Other Injectables of the Skin," Dermatologic Clinics 19(3): 491-508 (2001).

Giebler, FR "Fat Transplant to the Glabella and Forehead," Autologous Fat Transplantation (Marcel Decker, New York) Chapter 9, pp. 69-76 (2001).

Klein, AW "Substances for soft tissue augmentation," Dermatology Progress &Perspectives The Proceedings of the 18th World Congress of Dermatology, New York, Jun. 12-18, 1992 (Parthenon Publishing Group, New York) pp. 548-554 (1993).

Mustarde, JC "Plastic Surgery in Infancy and Childhood" (W.B. Saunders Co., Philadelphia) Chapter XVII, pp. 326-331 (1971).

Ashley, F. et al. "Augmentation of Surface Contour by Subcutaneous Injections of Silicone Fluid," Plastic & Reconstructive Surgery 51(1):8-13 (1973).

Klein, AW "Implantation technics for injectable collagen," J American Academy Dermatology 9(2):224-228 (1983).

* cited by examiner

METHODS OF ADMINISTERING A MATERIAL INTO A PATIENT FOR DERMAL ENHANCEMENT

RELATED APPLICATIONS

This application claims the benefit of U.S. Provisional Application No. 60/453,966 filed on Mar. 13, 2003, which is hereby incorporated by reference in its entirety.

FIELD OF THE INVENTION

The present invention relates to methods of administering a material to a patient for dermal enhancement and/or as soft tissue filler. The invention also relates to methods of molding a material to achieve a desired orientation of dermal enhancement and/or soft tissue filler. The invention also relates to the use of certain materials for the preparation of medical devices and pharmaceutical compositions for dermal enhancement and/or as soft tissue filler. The invention also relates to kits or packages that include a material for dermal enhancement and/or soft tissue filler and instructions as to how dermal enhancement or the filling of soft tissue is achieved.

BACKGROUND

It is often desired to improve irregularities of the skin and/or to manage facial lipoatrophy. The use of certain materials for these purposes is known. It would be beneficial, however, to provide improved methods of administering, sculpting and/or molding certain materials in order to achieve a desired orientation of administered material.

DETAILED DESCRIPTION OF THE INVENTION

The present invention relates to methods of administering a material to a patient for dermal enhancement of soft tissue and/or as soft tissue filler. The invention is further directed to methods of sculpting and/or molding a material to achieve a desired orientation of material that has been administered to a patient. The material may be, for example, a dermal enhancement and/or soft tissue filler material, including for example, a material comprising polylactic acid, hyaluronic acid, hydrogel, collagen and/or any other injectable material known to those skilled in the art, and optionally one or more additional ingredients. The invention is also directed to the use of a material for the preparation of a pharmaceutical composition for dermal enhancement or as soft tissue filler. The invention is further directed to kits comprising a material for dermal enhancement or as soft tissue filler and instructions as to how the dermal enhancement or soft tissue filling is to be achieved.

Figure 1:
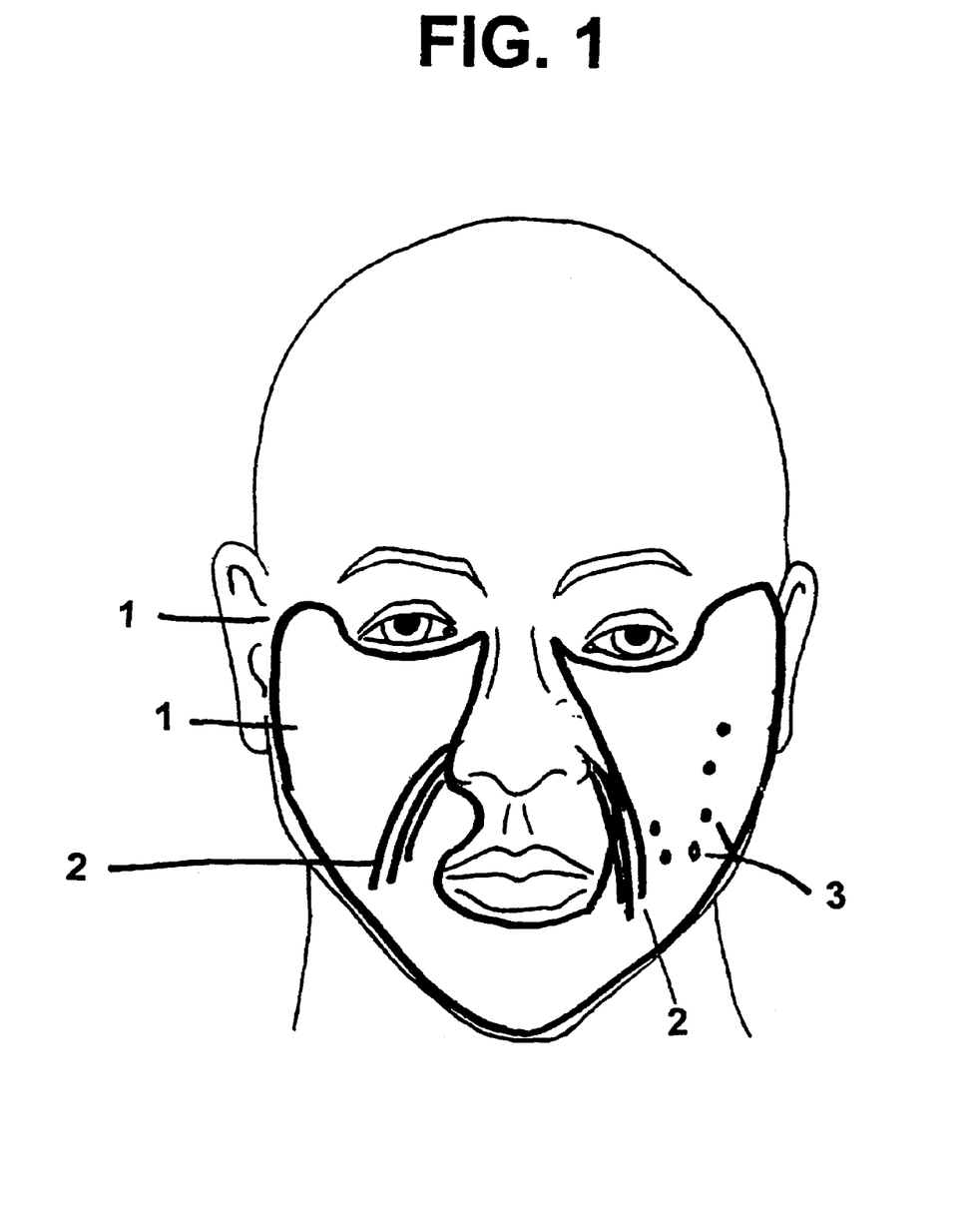
FIG. 1 depicts general areas on a patient's face, on which different methods of the present invention may be used.

FIG. 1 depicts general areas on a patient's face, on which different methods of the present invention may be used. FIG. 1 depicts the following: a general area (1) on a patient's face where a soft tissue fanning procedure or lattice injection technique may be used; a general area (2) on a patient's face where a parallel or layering technique may be used; and a general area (3) on a patient's face where a serial puncture or bolus technique may be used. The present invention is not limited to the use of particular techniques at the locations depicted on FIG. 1 or any other figures. The figures are only intended to be examples of places where the techniques according to the present invention may be utilized. The present invention is also not limited to administration to the face, but may include administration to any desired area of a patient.

The present invention is also not limited with respect to how much the patient is in need of the methods and/or uses set forth herein. By way of non-limiting example, the methods and uses of the present invention may benefit patients having any of the following degrees or stages of facial lipoatrophy: minimal fat wasting of the cheeks and/or minimal enhancement of the nasolabial folds; moderate fat wasting of the cheeks with enhancement of the nasolabial fold region, and appearance of the "nasolabial bands"; moderate fat wasting of the cheeks and temporal regions in addition to prominent nasolabial folds region "nasolabial bands"; and severe fat wasting and hallowing of the cheeks, temporal, and periocular regions in addition to visible facial bony prominences.

Materials administered to a patient in accordance with the present invention include, but are not limited to, those materials known to those skilled in the art, which may be administered to fill cavities in fat, and to treat a loss of subcutaneous fat such as lipoatrophy and dermal thinning. Dermal enhancement of soft tissue may be used to treat various conditions in the patient, including but not limited to, nasolabial folds, creases, wrinkles, fine lines, scars, acne scars or other depressions, stretch marks, and/or tissue wasting and the like. Materials used in accordance with the methods of the present invention also include, but are not limited to, those materials known to those skilled in that art that may be administered as soft tissue filler, which preferably increase tissue volume in desired areas of the patient. Examples of locations in which soft tissue filler may be used to increase tissue volume in a patient include, but are not limited to, administration into lips, and/or areas of lipoatrophy.

The methods of the present invention may be performed using any dermal enhancement and/or soft tissue filler materials available to those skilled in the art, such as autologous fat, hyaluronic acid, hydrogel, polylactic acid, collagen and the like. Accordingly, in the methods of the present invention, the material may be selected from, for example, one or more dermal enhancement and/or soft tissue filler materials comprising hyaluronic acid, hydrogel, collagen, and/or polylactic acid, and the like, and optionally one or more additional ingredients such as carriers and the like, as would be apparent to one skilled in the art. The material may be administered directly to a patient or may be used in forming a pharmaceutical composition by methods known in the art, using materials such as carriers or other excipients known in the art, for administration.

In certain embodiments, the material is a suspension that includes polylactic acid and optionally one or more additional ingredients such as carriers and the like. For example, the material may be NEW-FILLS® (Biotech Industry S.A.). Biotech Industry S.A. manufactures polylactic acid-containing fillers under various tradenames. This application is not limited, however, to a filler or material having any particular trade name, manufacturer or ingredient(s), but is meant to include any filler or material that may be administered in accordance with the purposes and methods described herein.

According to embodiments of the invention, a material for use as a dermal enhancement and/or soft tissue filler may be prepared in accordance with the methods described herein, or in accordance with the manufacturers' guidelines, or in the case of autologous material, the material is removed from the patient. For example, in embodiments where the material is a suspension that includes polylactic acid, it may be reconstituted as set forth in the examples below, which may be varied somewhat as would be apparent to those skilled in the art.

Methods of administering a material to a patient include injecting the material into the patient, for example, via a needle injection device. Other administration devices and methods known to those skilled in the art may be used in accordance with the present methods.

Patients in need of the present methods include those having any of the conditions described or mentioned herein or known to those skilled in the art, or patients desiring the effects achieved by the described methods.

According to certain methods of the invention, the patient's skin is cleansed, for example, by rubbing an effective surgical or antiseptic cleanser onto the skin to reduce or remove the level of bacteria on the skin surface. For example, the skin may be mechanically rubbed with a cleanser using a sterile gauze. The cleansing is performed in an area of the skin at and/or adjacent to any administration sites before administering any material to the patient. The cleanser may be allowed to set on the skin for several minutes.

Local and/or more general anesthesia may be administered to the patient before administering any material to the patient, in accordance with the present methods. Anesthetic options vary according to the procedure to be used. Local anesthesia may be administered to the patient to reduce the discomfort or sting associated with a needle or other injection. Examples of such local anesthesia include, but are not limited to, injectable 1% Xylocaine with or without epinephrine and with or without 8.4% sodium bicarbonate. By way of example, a 1:10 dilution of sodium bicarbonate to Xylocaine may be administered by methods known to those skilled in the art. Other forms of local anesthesia may be used as would be apparent to one of ordinary skill in the art, including for example, topical Betacaine® or other lidocaine-containing formulations.

A more general anesthesia may then be administered in the area to be treated. For example, a facial anesthesia may be administered to a patient having dermal enhancement and/or other treatment to their face. Examples of facial anesthesia include, but are not limited to, nerve blocks such as infraorbital nerve block, which may be administered for example, in the area of the nose, medial cheeks, upper lip and lower eyelid of a patient; and ring nerve blocks, which may be administered, for example, to the temporal region of a patient.

Figure 2:
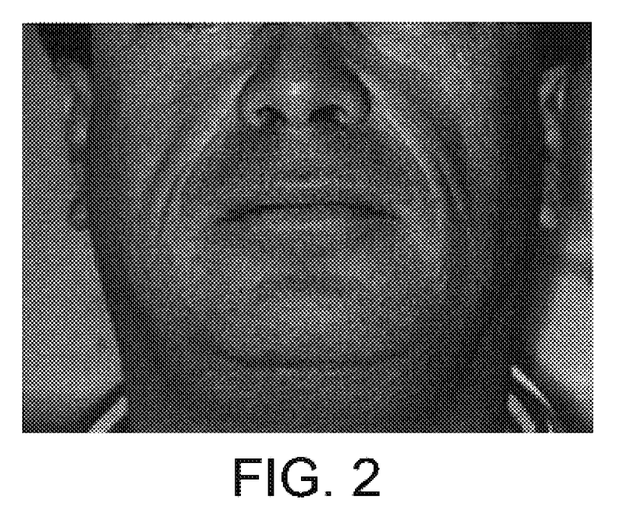
FIG. 2 depicts a patient before receiving dermal enhancement.
Figure 3:
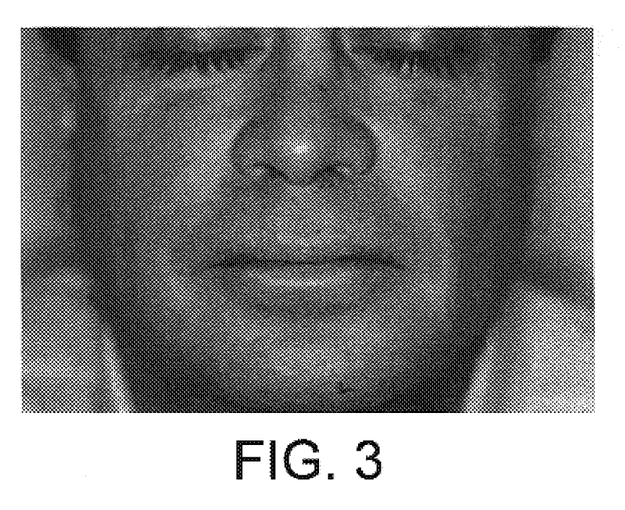
FIG. 3 depicts the patient of FIG. 2 after receiving dermal enhancement in accordance with the methods set forth herein.
Figure 4:
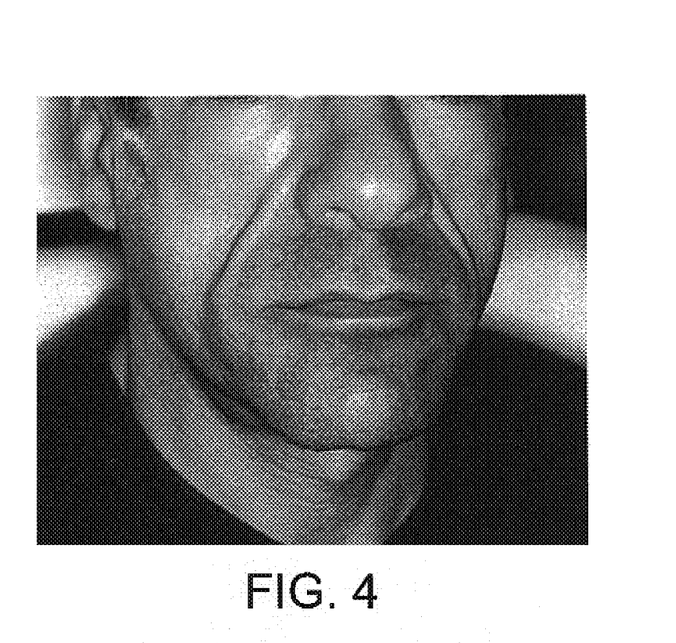
FIG. 4 depicts a patient before receiving dermal enhancement.
Figure 5:
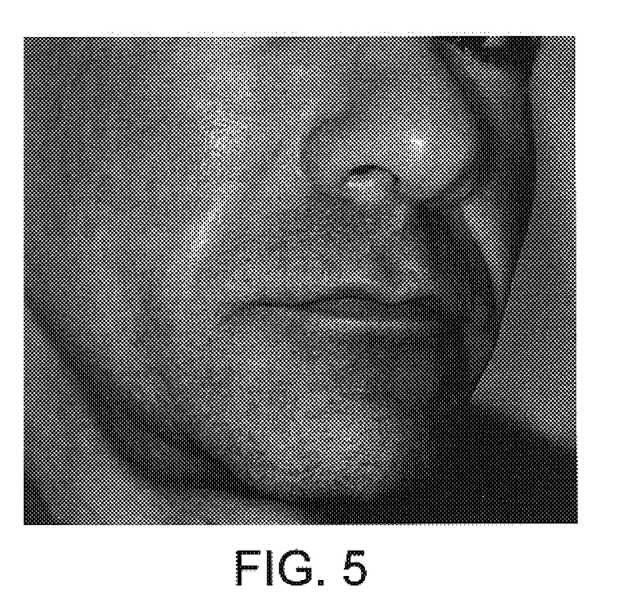
FIG. 5 depicts the patient of FIG. 4 after receiving dermal enhancement in accordance with the methods set forth herein.

FIG. 2 depicts a patient before receiving dermal enhancement. FIG. 3 depicts the same patient of FIG. 2 after receiving dermal enhancement in accordance with the methods set forth herein. FIG. 4 depicts a patient before receiving dermal enhancement. FIG. 5 depicts the same patient of FIG. 4 after receiving dermal enhancement in accordance with the methods set forth herein. The demonstrated results on the patients depicted in FIGS. 2-5 show that the methods of the present invention provide dermal enhancement to patients.

Dermal enhancement, soft tissue filling, and/or sculpting or molding of administered materials for dermal enhancement and/or soft tissue filling may be achieved by one or more of the following methods of the present invention. It should be recognized, however, that the methods, procedures and uses described herein may be used independently of one another. For example, after a method is used to administer a material in accordance with the present invention, the sculpting or molding technique of the present invention may be used and/or another sculpting and molding technique may be used as would be apparent to those skilled in the art. Conversely, the sculpting and molding methods of the present invention may be utilized regardless of whether the implemented injection technique is one of those described herein or another technique known to those skilled in the art.

Soft Tissue Fanning Procedure/Lattice Injection Technique

The present invention includes methods of administering a material to a patient, which include introducing a needle of a syringe containing a material to be administered through the epidermis of a patient into the dermis, subcutaneous and/or subcutaneous dermal junction. The bevel of the needle is optionally pointed down, i.e., toward the patient. The needle is then advanced approximately along a horizontal plane to the length of the needle. The material is injected substantially into the horizontal plane while the needle is being retracted out of the skin. The needle may be retracted such that a portion of the distal needle remains within the horizontal plane. For example, approximately ¼ inch may be retracted, thus leaving approximately ¼ inch of the distal needle (depending upon the size of the needle) within the horizontal plane.

In certain embodiments, the needle is guided and advanced at an angle of from about 10° to 20°, in certain embodiments of the invention the angle is about 15°, lateral to (in the horizontal plane) the prior injection. This procedure may be repeated about 2 to 5 times. According to certain embodiments, the procedure is repeated 3 or 4 times, with advancements increasing the angle, to form an approximately 45° angle between the furthest two injections. These methods are referred to as a "fanning procedure."

The present invention, therefore, includes methods of administering a material to a patient that include (a) providing a material to be administered in a syringe; (b) injecting a needle of the syringe into the patient at a first injection site; (c) advancing the needle into the patient approximately along a horizontal plane to the needle; (d) injecting at least a portion of the material substantially into the horizontal plane while retracting the needle, leaving a portion of the needle in the patient; (e) directing the needle to an angle of about 10° to 20° from the prior needle position; (f) repeating steps (c)-(e) one or more times; and (g) removing the needle from the patient. This set of injections of material from a first injection site is a first fanning of the material being injected. Naturally, it is contemplated that step (e) may be performed at angles less than 10°, such as 5 to 10°. Moreover, mechanical devices for multiple injections or single injections at various angles around the point of injection are embodiments within the ambit of the invention.

According to certain embodiments, the portion of material injected in step (d) may be about ¼ of the desired amount of material to be administered to the first injection site; and the repeating step (f) is performed three times, such that ¼ of the desired amount of material to be administered to the first injection site is injected each of four times.

According to other embodiments, the repeating step (f) is performed three times, and the directing of the needle in each repetition is to an angle about 15° from each prior injection, such that the fourth injection is about 45° from the first injection.

The fanning procedure may be performed one or more additional times to produce an overlapping lattice technique. According to certain embodiments using the overlapping lattice technique, after the desired angle (e.g., approximately 45° angle) is reached, the needle is retracted from the skin and the procedure may be repeated as necessary starting with a new injection site. The new injection site may be approximately 0.5 to 2 centimeters, or approximately 1 centimeter from the previous injection site.

Thus, the methods of the present invention may further include (h) injecting a needle of the syringe into the patient at a second injection site; (i) advancing the needle into the patient approximately along a horizontal plane to the needle; (j) injecting at least a portion of the material substantially into the horizontal plane while retracting the needle, leaving a portion of the needle in the patient; (k) directing the needle to an angle of about 5° to 20° or about 10° to 20° from the prior injection; (l) repeating steps (i)-(k) one or more times; and (m) removing the needle from the patient. This repetition of the fanning from a second injection site may overlap with the fanning from the first injection site to begin forming a lattice. Further steps (h)-(m) may be repeated one or more additional times, such that injections are made into third, fourth, and/or fifth injection sites or more, forming a lattice from each of the overlapping fanning patterns.

Figure 6:
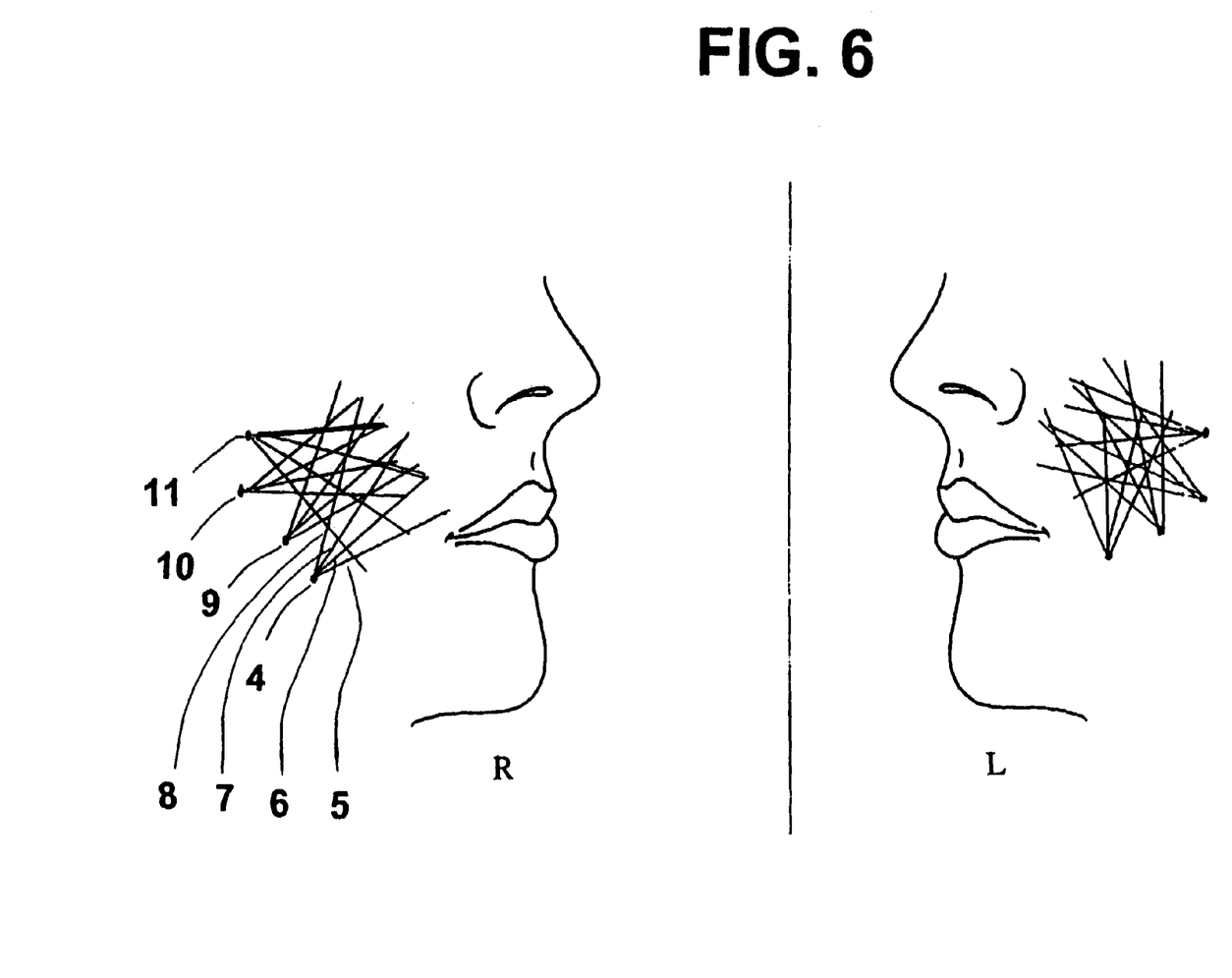
FIG. 6 depicts possible angles and advancements in accordance with certain embodiments of soft tissue fanning methods in accordance with the present invention.
Figure 7:
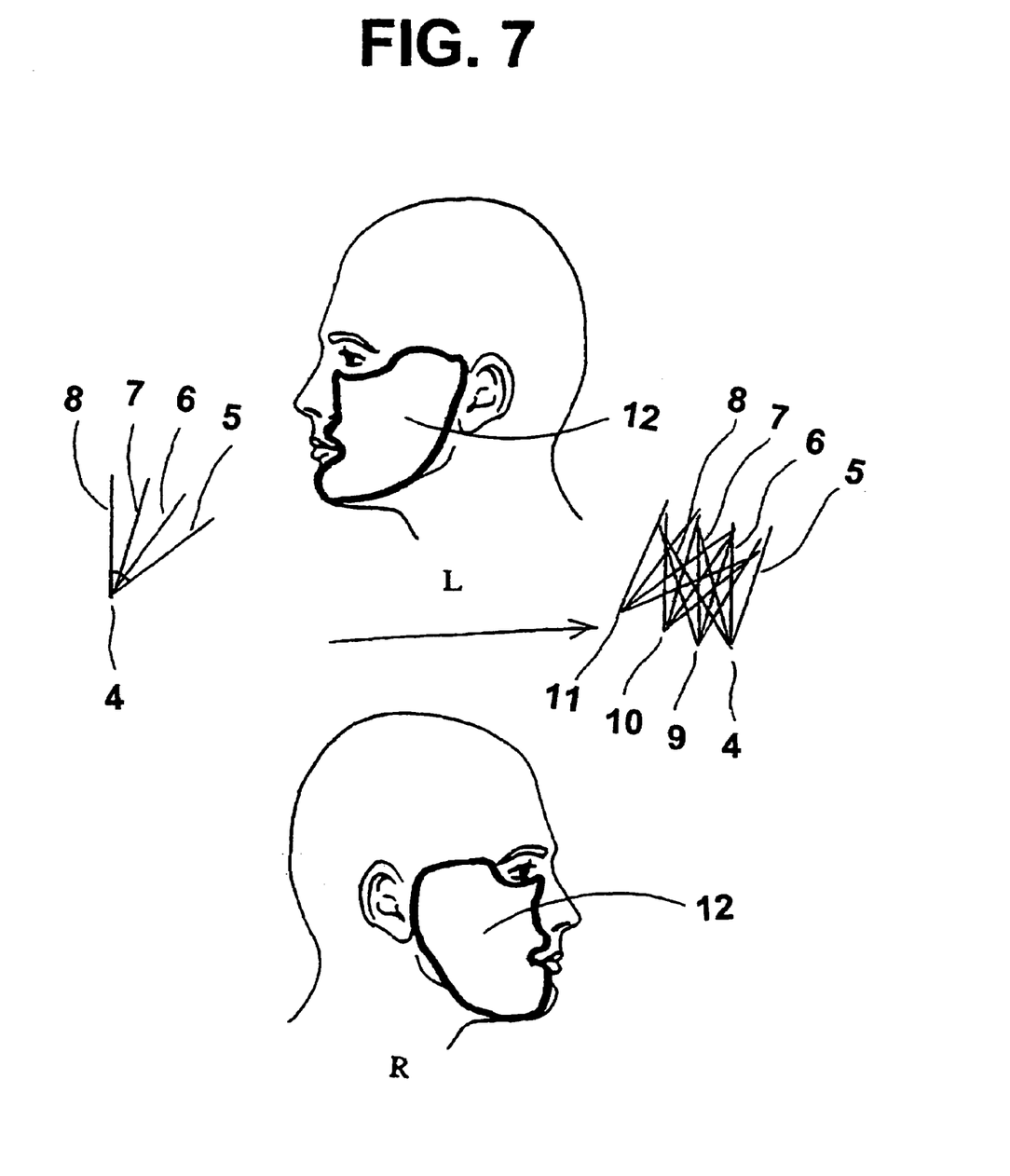
FIG. 7 depicts possible angles, advancements and injection locations on a patient's face in accordance with certain embodiments of soft tissue fanning methods in accordance with the present invention.

Non-limiting examples of possible angles, needle advancements and injection locations according to certain embodiments of fanning and lattice techniques of the invention are depicted in FIGS. 6 and 7. In particular, a needle is injected for example at site (4) on the patient. The needle is then advanced (5) approximately along the horizontal plane to the length of the needle. The material is injected substantially into the horizontal plane while the needle is being retracted approximately three quarters of the way (e.g., 1¼ inches) out of the skin, thus leaving approximately one quarter (e.g., ¼ inch) of the distal needle (depending upon the size of the needle) approximately within the horizontal plane. This procedure is repeated about 2 to 5 times. The needle is guided and advanced (6), (7), and (8) each time at an angle of about 10° to 20° from the previous injection.

After the desired advancements and injections are complete fanning out from the first injection site (4), the needle is retracted from the skin and the procedure may be repeated beginning at a new injection site (9), which may be approximately 0.5 to 2.0 centimeters from the previous injection site (4). The fanning procedure is repeated from the new injection site (9). The needle is retracted from the skin and the procedure may be repeated one or more times beginning at new injection sites (10) and (11).

The fanning methods of the present invention may be used at various locations on a patient including, for example, at locations (1) depicted on FIG. 1 and at location (12) depicted on FIG. 7.

The present invention is further directed to the use of a suitable material for the preparation of a pharmaceutical composition for dermal enhancement, wherein dermal enhancement is achieved by (a) providing the material to be administered in a syringe; (b) injecting a needle of the syringe into a patient at a first injection site; (c) advancing the needle into the patient approximately along a horizontal plane to the needle; (d) injecting at least a portion of the material substantially into the horizontal plane while retracting the needle, leaving a portion of the needle in the patient; (e) directing the needle to an angle of about 5° to 20° or about 10° to 20° from the prior needle position; (f) repeating steps (c)-(e) one or more times; and (g) removing the needle from the patient. The suitable material may include any material known to those skilled in the art, including, but not limited to polylactic acid, hydrogel, hyaluronic acid, and/or collagen.

These uses may further include (h) injecting a needle of the syringe into the patient at a second injection site; (i) advancing the needle into the patient approximately along a horizontal plane to the needle; (j) injecting at least a portion of the material substantially into the horizontal plane while retracting the needle, leaving a portion of the needle in the patient; (k) directing the needle to an angle of about 10° to 20° from the prior injection; (l) repeating steps (i)-(k) one or more times; and (m) removing the needle from the patient. Additionally, steps (h)-(m) may optionally be repeated one or more additional times.

Parallel and Layering Technique for Creases, Fine Lines, Wrinkles, Nasolabial Folds, Vermillion Border, Lips, Striae and the Like According to additional embodiments of the present invention, parallel technique methods are provided in which a syringe containing material to be administered is advanced into a patient with a needle approximately along the horizontal plane to the length of the area in need of soft-tissue enhancement or the length of the needle, for example a 25 gauge, 1½ inch needle. Material is injected substantially into the horizontal plane as the needle is retracted out of the patient. The needle is then inserted in the patient in another adjacent location and advanced substantially parallel to the prior injection track. Material is injected substantially into the horizontal plane to the length of the area in need of soft tissue enhancement or the length of the needle, as the needle is retracted out of the patient. The process of injecting into a new site of the patient, advancing the needle substantially parallel to prior injection tracks, and withdrawing the needle while injecting material into the patient, is repeated as many times as desired or necessary until the desired dermal enhancement is achieved.

Therefore, the present invention provides methods of administering a material to a patient, which include (a) providing a material to be administered in a syringe; (b) injecting a needle of the syringe into the patient at a first injection site; (c) advancing the needle into the patient approximately along a horizontal plane to an area in need of soft-tissue enhancement forming a needle track; (d) injecting at least a portion of the material substantially into the horizontal plane while retracting the needle; and optionally repeating (b)-(d) one or more times at other injection sites, wherein the needle is advanced substantially parallel to at least one prior injection track, until the desired dermal enhancement is achieved.

Figure 8:
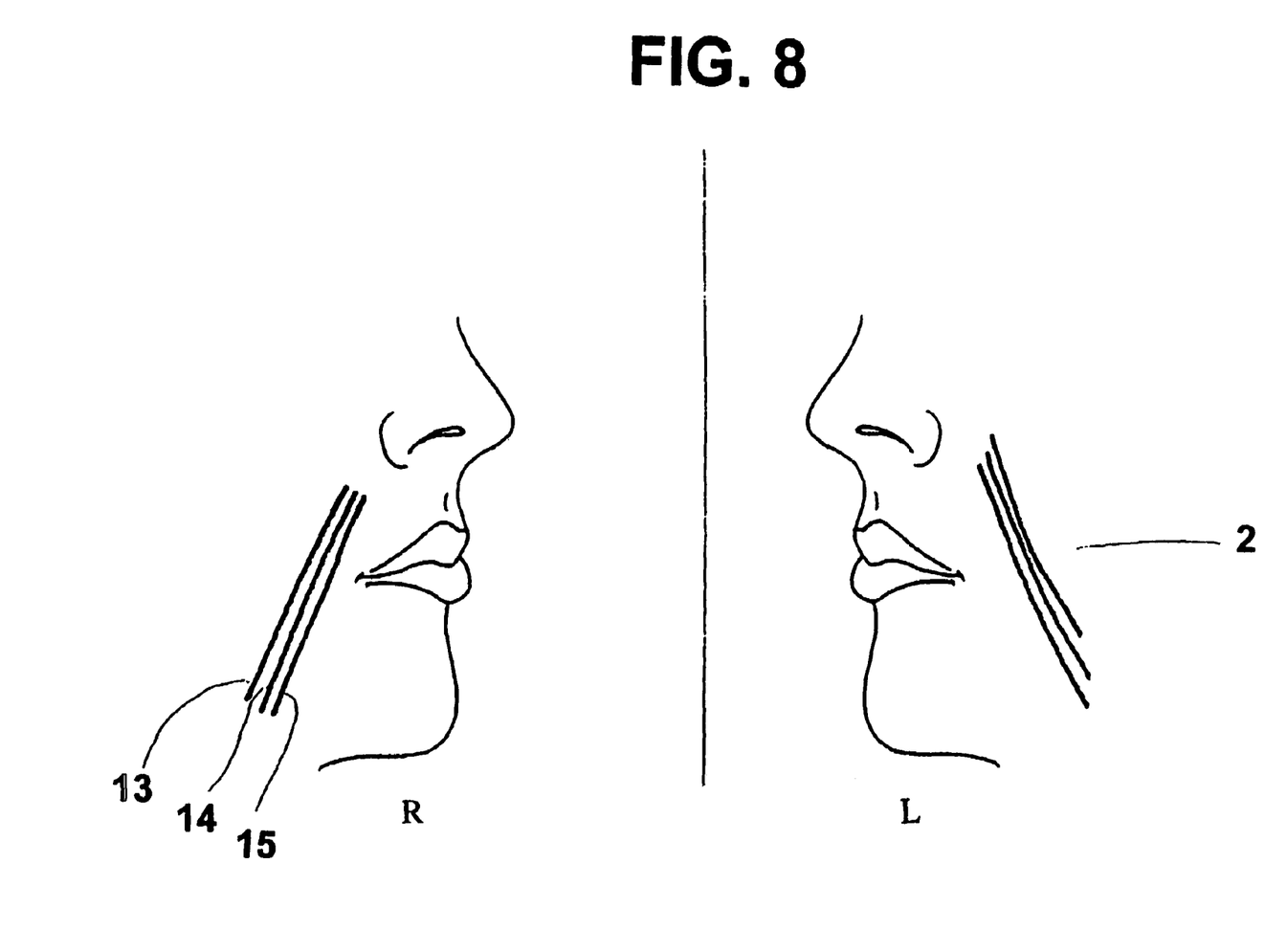
FIG. 8 depicts general areas on a patient's face, on which parallel technique methods of the present invention may be used.

The parallel methods of the present invention may be used at various locations on a patient including, for example, the locations (2) of a patient's face depicted on FIGS. 1 and 8. As shown in FIG. 8, according to these methods a syringe containing material to be administered may be advanced into a patient along line (13) with a needle approximately along the horizontal plane to the length of the area in need of soft-tissue enhancement or the length of the needle. The material is injected substantially into the horizontal plane (13) as the needle may be retracted out of the patient. This procedure may be repeated one or more times as desired, for example along lines (14) and/or (15) of FIG. 8 depending on the desired effect, patient to be treated, etc.

The present invention is further directed to the use of a suitable material for the preparation of a pharmaceutical composition for dermal enhancement, wherein dermal enhancement is achieved by (a) providing a material to be administered in a syringe; (b) injecting a needle of the syringe into the patient at a first injection site; (c) advancing the needle into the patient approximately along a horizontal plane to an area in need of soft-tissue enhancement forming a needle track; (d) injecting at least a portion of the material substantially into the horizontal plane while retracting the needle; and optionally repeating (b)-(d) one or more times at other injection sites, wherein the needle is advanced substantially parallel to at least one prior injection track, until the desired dermal enhancement is achieved. The suitable material may include any material known to those skilled in the art, including, but not limited to polylactic acid, hydrogel, hyaluronic acid, and/or collagen.

According to another embodiment of the present invention, layering technique methods are provided in which a syringe containing material to be administered is advanced into a patient from a first injection site with a needle approximately along the horizontal plane to the length of the area in need of soft-tissue enhancement or the length of the needle, for example a 25 gauge, 1½ inch needle. Material is injected substantially into the horizontal plane as the needle is retracted such that a portion of the distal needle remains within the patient, thus not withdrawing the needle from the first injection site. According to certain embodiments, the needle is retracted out approximately three quarters of the length of the needle (e.g., 1¼ inches) leaving approximately one quarter (e.g., ¼ inch depending on the size of the needle) of the distal needle tip within the desired plane.

The needle is then pointed at a different angle with respect to the patient, such as a steeper angle downward into the patient, and the needle is advanced into the patient. The material is injected substantially into a second horizontal plane to the length of the area in need of soft tissue enhancement, as the needle is retracted much of the way out of the patient again. The process may be repeated one or more times to achieve the desired effect, each time leaving a portion of the distal needle within the patient, pointing the needle at a different angle into the patient and injecting material into each new horizontal plane. After the desired injections are complete, the needle is fully retracted out of the patient. The entire process may be optionally repeated one or more times beginning at a new injection site each time.

Therefore, the present invention provides methods of administering a material to a patient which include (a) providing a material to be administered in a syringe; (b) injecting a needle of the syringe into the patient at a first injection site; (c) advancing the needle into the patient approximately along a horizontal plane to an area in need of soft-tissue enhancement; (d) injecting at least a portion of the material substantially into a first horizontal plane while retracting the needle, leaving a portion of the needle in the patient; (e) directing the needle to an angle of about 10 to 25° with respect to the patient from the prior needle position; (f) advancing the needle into the patient; (g) injecting material substantially into a second horizontal plane while retracting the needle; and (h) removing the needle from the patient. The directing, advancing, and injecting, i.e., (e)-(g), may be repeated one or more times into respective horizontal planes until a desired dermal enhancement is achieved before removing the needle. The methods optionally include inserting the needle into the patient at one or more new injection sites and repeating the method at the new injection sites.

Figure 9:
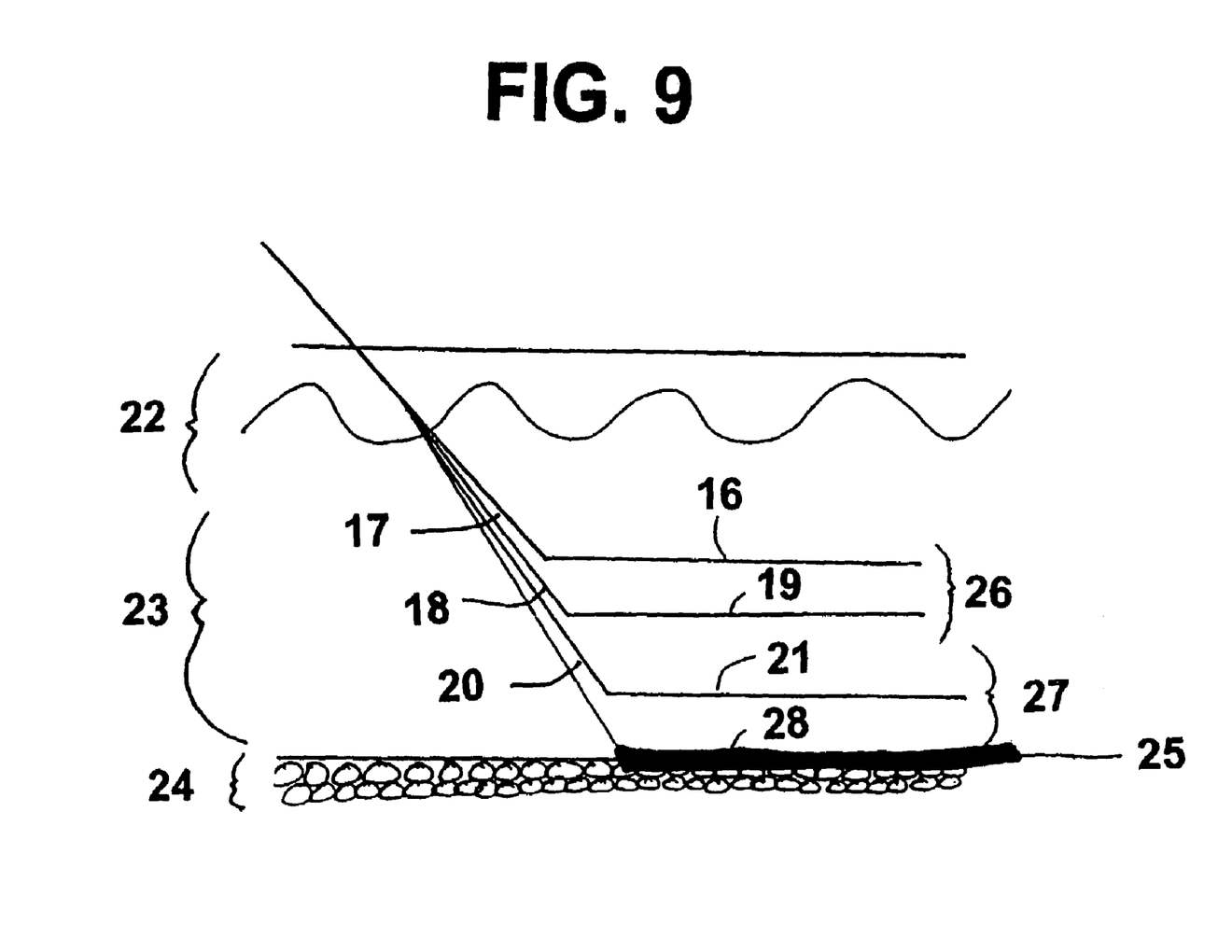
FIG. 9 depicts possible general angles of insertion into a patient's skin according to certain embodiments of layering methods in accordance with the present invention.

The layering methods of the present invention may be used at various locations on a patient including, for example, the locations (2) of a patient's face depicted on FIGS. 1 and 8. As shown in FIG. 8, according to these methods a syringe containing material to be administered may be advanced into a patient along line (13) with a needle approximately along the horizontal plane to the length of the area in need of soft-tissue enhancement or the length of the needle. As depicted in FIG. 9, the material is injected substantially into a first horizontal plane (16) as the needle is retracted leaving a portion of the needle in the patient. The angle of the needle is then changed from a first injection angle (17), to a second injection angle (18). The material is injected substantially into a second horizontal plane (19) resulting from the second injection angle (18). This procedure may be repeated one or more times as desired, depending on the desired effect, patient to be treated, etc. For example, the needle may be advanced along line (20) and material injected substantially horizontal plane is along line (21), and so forth. FIG. 9 depicts that the needle is advanced through epidermis (22) before injecting material into the dermis (23). According to certain embodiments, one or more of the injections may take place in the subcutaneous (24) layer and/or at the subcutaneous dermal junction (25). According to certain embodiments, at least one injection is made into the mid dermis (26) (e.g., injections (16) and (19)), at least one injection is made into the lower dermis (27) (e.g., injection (21)), and at least one injection is made substantially at the subcutaneous dermal junction (25) (e.g., injection (28)).

The present invention is further directed to the use of a suitable material for the preparation of a pharmaceutical composition for dermal enhancement, wherein dermal enhancement is achieved by (a) providing a material to be administered in a syringe; (b) injecting a needle of the syringe into a patient at a first injection site; (c) advancing the needle into the patient approximately along a horizontal plane to an area in need of soft-tissue enhancement; (d) injecting material substantially into a first horizontal plane while retracting the needle, leaving a portion of the needle in the patient; (e) directing the needle to an angle of about 1° to 25° with respect to the patient from the prior needle position; (f) advancing the needle into the patient; (g) injecting material substantially into a second horizontal plane while retracting the needle; and (h) removing the needle from the patient. Steps (e)-(g) may be repeated one or more times before removing the needle, until a desired dermal enhancement is achieved. The suitable material may include any material known to those skilled in the art, including, but not limited to polylactic acid, hydrogel, hyaluronic acid, and/or collagen.

Serial Puncture/Bolus Technique for Acne Scars or Other Depressions

According to other embodiments of the present invention, methods are provided in which a needle is advanced at an angle of about 45° to 90° into the dermis, subcutaneous and/or subcutaneous dermal junction of the patient over, or substantially adjacent to, an acne scar or other depression in the patient. Material is injected from the needle into the patient, while the needle is optionally advanced into and/or retracted from the patient until the desired dermal enhancement is achieved. The needle is then completely retracted from the skin and may be injected into, or adjacent to, another depression.

Accordingly, the present invention provides methods of administering a material to a patient, which include (a) providing in a syringe a material to be administered to the patient;

(b) injecting a needle of the syringe into the patient at a first injection site, wherein the needle is at an angle of about 45° to 90° to the dermis; (c) injecting at least a portion of the material into the patient until desired dermal enhancement is achieved; and (d) removing the needle from the patient. While the material is being injected into the patient, the needle may be advanced into and/or retracted from the patient. The first injection site may substantially at, or adjacent to, the site of a scar or other depression.

The serial puncture/bolus methods of the present invention can be used for example, on acne scars or other depressions on various portions of a patient including, for example, on a patient's face as depicted on FIG. 1 at for example, locations (3).

The present invention is further directed to the use of a suitable material for the preparation of a pharmaceutical composition for dermal enhancement, wherein dermal enhancement is achieved by (a) providing in a syringe a material to be administered to a patient; (b) injecting a needle of the syringe into the patient at a first injection site, wherein the needle is at an angle of about 45° to 90° to the dermis; (c) injecting at least a portion of material into the patient until desired dermal enhancement is achieved; and (d) removing the needle from the patient. The suitable material may include any material known to those skilled in the art, including, but not limited to polylactic acid, hydrogel, hyaluronic acid, and/or collagen.

Sculpturing and Molding Technique

According to other embodiments of the present invention, methods are provided for sculpturing and/or molding material that has been injected into a patient.

According to certain embodiments of these methods, they are double glove methods using a pair of gloves larger than one's normal size gloves, and a pair of gloves approximately the normal size for the user. The double-gloved hand may be either the non-dominant or dominant hand. A larger inner glove is first placed on the hand. The inner glove may be either sterile or non-sterile. One or more metal fingertip plates, thimbles, or the like may then be placed on one or more fingertips over the gloved hand. By way of non-limiting example, one or more metal fingertip plates, thimbles, or the like are placed on the thumb, index and/or third fingertips over the gloved hand.

An outer glove (from the smaller or approximately normal size pair of gloves), which may be sterile for example in the case where the outer glove comes into contact with the patient, is then placed over the inner glove and fingertip plates or thimbles. The configuration of the larger inner glove, fingertip plates or thimbles and smaller outer glove allows for a rolling pin maneuver of the fingertip plates or thimbles, which may be rolled over the inner glove, for example to mold and/or sculpt material that has been injected into a patient. According to certain embodiments, the fingers, palm, thenar eminence and/or other parts of the gloved hand may be used in accordance with these methods to perform molding and/or sculpting. Molding can be completed for example, within about 60 minutes.

Accordingly, the present invention includes methods of molding material that has been administered to a patient. These methods include administering material to a patient; and molding the material by applying pressure with one or more hands of a person to various portions of the patient's dermis substantially above the injected material until a desired orientation of the material within the patient is achieved; wherein at least one of the person's hands is double-gloved by a method that includes applying a first glove larger than the person's glove size to the hand to provide a gloved hand, placing a hard object such as a fingertip plate or thimble on at least one digit over the gloved hand, and placing a second glove that is smaller than the first glove over the hand. Also contemplated in the invention are sterile or aseptic gloves with fingertip plates or thimbles that can be used in the aforementioned procedure. Naturally, hard plastic fingertips or fingertips comprising other hard materials can replace one or more of the metal fingertips.

An advantage of the double glove method and fingertip plates is that it may protect the fingertips of the physician from accidental needle injuries.

The present invention is further directed to the use of a suitable material for the preparation of a pharmaceutical composition for dermal enhancement, wherein dermal enhancement is achieved by administering the material to a patient; and molding the material by applying pressure with one or more hands of a person to various portions of the patient's dermis substantially above the administered material until a desired orientation of the material within the patient is achieved. In these embodiments, at least one of the person's hands is double-gloved by a method that includes applying a first glove larger than the person's glove size the hand to provide a gloved hand, placing a hard object such as a fingertip plate or thimble on at least one digit over the gloved hand, and placing a second glove that is smaller than the first glove over the hand. Pressure may be applied for example by using the fingers, thumb, palm, thenar eminence and/or any part of the hand for molding and/or sculpting the material.

The present invention is further directed to kits or packages, which include one or more suitable materials that may either be administered directly or formed into a pharmaceutical composition for dermal enhancement or as a soft tissue filler, and instructions that dermal enhancement or soft tissue filling is achieved by any of the methods described herein. The suitable material may include any material known to those skilled in the art, including, but not limited to polylactic acid, hydrogel, hyaluronic acid, and/or collagen.

After performing any of the methods of the present invention, the skin of the patient at, adjacent to, and surrounding the treated area can be gently cleansed with a facial cleanser, alcohol, or hydrogen peroxide, and/or a topical antibiotic cream/ointment can be applied.

Depending on the patient, material or soft tissue filler product used, type of enhancement sought, and method used, in certain circumstances it may be advantageous to repeat dermal enhancement sessions about every 4-8 weeks. The time period, however, may be less or greater than the 4-8 weeks, as to be determined by the a physician or other treating person.

The following examples illustrate specific embodiments of the invention. The examples set forth herein are meant to be illustrative and should not in any way serve to limit the scope of the claimed invention. As would be apparent to skilled artisans, various changes and modifications are possible and are contemplated within the scope of the invention described.

EXAMPLES

Example 1

Pretreatment Preparation and Safety

Office staff should first be educated that they may potentially be exposed to infectious material, particularly blood bourn agents. All personnel who may come in contact with blood should be vaccinated against hepatitis B. All personnel should also be advised of the necessity of informing their supervisor if a needle stick injury or other exposure to blood occurs.

Basic safety precautions should be adhered to throughout the procedure, including the use of surgical gloves and the use of barrier clothing, such as gowns, face masks, and eye protection; and sharps and all contaminated drapes and other hazardous material should be disposed of by hazardous waste removal companies. Disposable syringes and needles should be placed in puncture-resistant containers for disposal, which containers are preferably located as close as practical to the use area.

Although saliva has not been implicated in any transmittal disease, to minimize the need for emergency mouth-to mouth resuscitation, mouthpiece resuscitation bags, or other ventilation devices should be available for use in areas in which the need for resuscitation is predictable.

Reconstitution

NEW-FILL® (Biotech Industry S.A.) is reconstituted by the following method, which differs from the manufacturer's guidelines. However, fillers prepared according to manufacturers guidelines are also included within the scope of the present invention. A sterile 3 cc syringe with an 18 gauge, ½ inch sterile needle is used to withdraw at least 4 ml-6 ml of Bacteriostatic water. Other sized syringes and/or needles may be used in accordance with the invention. The dry contents of the NEW-FILL® vial are then shaken. The vial cap is removed and about 4 ml-6 ml of Bacteriostatic water is slowly added to the dry powder by introducing the 18 gauge, ½ inch needle into the rubber bung of the vial. The vacuum from the vial is allowed to draw the Bacteriostatic water into the NEW-FILL® vial. The vial is allowed to stand for at least 90 minutes to allow the contents to slowly dissolve and to allow the formation of covalent bonds. The reconstituted vial is not shaken until the contents of the vial have fully dissolved. After about 90 minutes, the vial is shaken continuously until a homogeneous translucent hydrogel suspension is obtained. Reconstituted hydrogel should be stored at room temperature and environment until used.

Skin Preparation

An antiseptic cleanser is mechanically rubbed onto the patient's skin on and near the area to be treated, with sterile gauze, to attempt to reduce the bacteria on the skin surface. The cleanser is allowed to set on the skin for several minutes for optimal effect.

Local Anesthesia

A 1:10 dilution of sodium bicarbonate to Xylocaine is administered, as a neutralization process, to diminish the discomfort and sting with injection. A facial anesthesia is then achieved via nerve blocks and/or topical anesthetic preparations.

Soft Tissue Enhancement/Molding

Soft tissue enhancement and/or molding are achieved by one or more of the techniques set forth in Examples 2-6 described below.

Repeated Soft Tissue Enhancement/Molding Sessions

Hydrogel soft tissue enhancement may be repeated every 4-8 weeks. Less hydrogel may be necessary upon subsequent treatment sessions. Dermal enhancement and remodeling may be evident at two months from the prior injection session.

Postoperative Care

The skin of the patient adjacent to and surrounding the treated area is gently cleansed with a facial cleanser, alcohol, or hydrogen peroxide, and a topical antibiotic cream/ointment is applied. Ice may optionally be applied to the skin of the patient adjacent to and surrounding the treated area.

Example 2

Soft Tissue Fanning Procedure/Lattice Injection Technique

About 2.5 to 3.0 cc of reconstituted hydrogel is contained in a 3 cc syringe. This size syringe was selected for leverage purposes, but other size syringes may be used in accordance with the present invention in each of the examples described herein. With the bevel of a 25 gauge, 1½ inch needle pointed down, the needle of the syringe containing reconstituted hydrogel is introduced through the epidermis into the desired tissue plane. The needle is then advanced approximately along the horizontal plane to the length of the 25 gauge, 1½ inch needle. Hydrogel is injected substantially into the horizontal plane as the needle is retracted about 1¼ inch out of the skin, thus leaving about ¼ inch of the distal needle approximately within the horizontal plane. The needle is guided and advanced at an approximately 15° angle lateral to (in the horizontal plane) the prior injection. This procedure is repeated with 3 advancements to form an approximately 45° angle from the first injection. The needle is retracted from the skin and the procedure is repeated about 1 cm from the previous entry point.

Example 3

Parallel Technique for Creases; Fine Lines; Wrinkles; Nasolabial Folds; Vermillion Border; Lips; Striae About 2.5 to 3.0 cc of reconstituted hydrogel is contained in a 3 cc syringe. However, as with all of the examples, different size syringes and needles may be used. A 25 gauge, 1½ inch needle is inserted into a patient at a first injection site and advanced into the patient with a needle approximately along the horizontal plane to the length of the area in need of dermal enhancement or the length of the needle. The hydrogel is injected substantially into the horizontal plane as the needle is retracted out of the patient. The needle is then inserted into the patient at a second injection site. The needle is advanced substantially parallel to the prior injection track. Material is injected substantially into the horizontal plane as the needle is retracted out of the patient. The injecting process is repeated at new injection sites until the desired soft tissue enhancement is achieved.

Example 4

Layering Technique for Creases; Fine Lines; Wrinkles; Nasolabial Folds; Vermillion Border; Lips; Striae and the Like About 2.5 to 3.0 cc of reconstituted hydrogel is contained in a 3 cc syringe. A 25 gauge, 1½ inch needle is advanced into the patient with a needle approximately along the horizontal plane to the length of the area in need of dermal enhancement or the length of the needle. Hydrogel is injected substantially into a first horizontal plane as the needle is retracted out approximately ¼ inches leaving approximately ¼ inch of the distal needle tip within the soft tissue.

The needle is then directed to at a different angle with respect to the dermis, such as a steeper angle toward the patient and the needle is advanced into the patient. Material is injected substantially into a second horizontal plane as the needle is retracted out approximately ¼ inches, again leaving approximately ¼ inch of the distal needle tip within the soft tissue. The needle angle is changed and material is injected into different horizontal planes with respect to the dermis of the patient until desired soft tissue enhancement is achieved.

Example 5

Serial Puncture/Bolus Technique for Acne Scars or Other Depressions

Hydrogel is injected into a patient using a 1.0 cc syringe 26 gauge, ½ inch needle. The needle is advanced at an angle of about 45° to 90° into the dermis over, or substantially adjacent to, the depression. Material is injected into the patient until a desired dermal enhancement is achieved. The needle is completely retracted from the skin and then injected into, or substantially adjacent to, another depression.

Example 6

Sculpturing and Molding Technique

A double-gloved procedure is performed using a pair of sterile or non-sterile gloves a size larger than one's normal size gloves and a pair of about normal size sterile gloves. A larger inner glove is placed on a hand of a physician first. One or more metal fingertip plates or thimbles are placed on one or more of the thumb, or fingertips over the non-dominant gloved hand. The outer glove (about one's normal size glove) is then placed over the first glove and metal fingertip plates. A rolling pin maneuver of the metal fingertip plates are rolled over the inner glove to mold and sculpt hydrogel that has been administered to a patient. Molding is completed within about 60 minutes.

I claim:

1. A method of administering a material to a patient, comprising:
    (a) providing a material to be administered in a syringe;
    (b) injecting a needle of the syringe into the patient at a first injection site;
    (c) advancing the needle into the patient approximately along a horizontal plane with respect to epidermis of the patient;
    (d) injecting at least a portion of the material substantially into the horizontal plane while retracting the needle, leaving a portion of the needle in the patient;
    (e) directing the needle to an angle of about 5° to 20° from the prior needle position;
    (f) repeating (c)-(e) one or more times;
    (g) removing the needle from the patient;
    (h) injecting the needle of the syringe into the patient at a second injection site;
    (i) advancing the needle into the patient approximately along a horizontal plane with respect to the epidermis of the patient;
    (j) injecting at least a portion of the material substantially into the horizontal plane while retracting the needle, leaving a portion of the needle in the patient;
    (k) directing the needle to an angle of about 5° to 20° from the prior injection;
    (l) repeating steps (i)-(k) one or more times; and
    (m) removing the needle from the patient;
    wherein said method recontours skin of the patient by dermal or soft tissue enhancement.

2. The method of claim 1, wherein the repeating step (f) is performed three times, and the directing of the needle in each repetition is to an angle about 15° from each prior injection, such that the fourth injection is about 45° from the first injection.

3. The method of claim 1, comprising repeating (h)-(m) one or more additional times.

4. The method of claim 1, wherein the second injection site is approximately 0.5 to 2 cm from the first injection site.

5. The method of claim 1, wherein the material is soft tissue filler.

6. The method of claim 1, wherein the material is a dermal enhancement material.

7. The method of claim 1, wherein the material comprises at least one material selected from the group consisting of hyaluronic acid, hydrogel, collagen, and polylactic acid.

8. The method of claim 1, wherein the material comprises polylactic acid.

9. A method of administering a material to a patient, comprising:
    (a) providing a material to be administered in a syringe;
    (b) injecting a needle of the syringe into the patient at a first injection site;
    (c) advancing the needle into the patient approximately along a horizontal plane with respect to an epidermis of the patient, to an area in need of soft-tissue enhancement;
    (d) injecting at least a portion of the material substantially into the horizontal plane while retracting the needle; and
    (e) removing the needle from the patient;
    further comprising repeating (b)-(d) at least one additional time at one or more injection sites, wherein the needle is advanced substantially parallel to at least one prior injection;
    wherein said method recontours skin of the patient by dermal or soft tissue enhancement.

* * * * *